(12) United States Patent
Utely et al.

(10) Patent No.: US 6,277,116 B1
(45) Date of Patent: Aug. 21, 2001

(54) SYSTEMS AND METHODS FOR SHRINKING COLLAGEN IN THE DERMIS

(75) Inventors: David Utely, San Carlos; Stuart Edwards, Portola Valley; Richard Goode, Los Altos, all of CA (US)

(73) Assignee: VidaDerm, Sunnyvale, CA (US)

( * ) Notice: Subject to any disclaimer, the term of this patent is extended or adjusted under 35 U.S.C. 154(b) by 0 days.

(21) Appl. No.: 09/251,554

(22) Filed: Feb. 17, 1999

Related U.S. Application Data

(63) Continuation-in-part of application No. 08/637,095, filed on Apr. 24, 1996, which is a continuation of application No. 08/389,924, filed on Feb. 16, 1995, now Pat. No. 5,569,242, which is a continuation of application No. 08/238,862, filed on May 6, 1994, now Pat. No. 5,458,596.

(51) Int. Cl.$^7$ ................................................ A61B 18/18
(52) U.S. Cl. ............................... 606/42; 606/41; 606/50; 607/102; 607/109
(58) Field of Search ................................. 606/41, 42, 44, 606/48–50, 9; 607/115, 99–104, 108, 109, 139, 140, 148, 152, 153

(56) References Cited

U.S. PATENT DOCUMENTS

| | | | |
|---|---|---|---|
| 5,374,283 | * 12/1994 | Flick | 607/46 |
| 5,569,242 | * 10/1996 | Lax et al. | 606/42 |
| 5,588,960 | * 12/1996 | Edwards et al. | 604/20 |
| 5,769,846 | * 6/1998 | Edwards et al. | 606/41 |
| 5,843,078 | * 12/1998 | Sharkey | 606/41 |
| 5,868,744 | * 2/1999 | Willmen | 606/50 |
| 5,919,188 | * 7/1999 | Shearon et al. | 606/41 |
| 6,010,500 | * 1/2000 | Sherman et al. | 606/41 |
| 6,030,384 | * 2/2000 | Nezhat | 606/48 |
| 6,068,629 | * 5/2000 | Haissaguerre et al. | 606/41 |
| 6,068,653 | * 5/2000 | LaFontaine | 607/116 |
| 6,077,257 | * 6/2000 | Edwards et al. | 604/506 |
| 6,081,749 | * 6/2000 | Ingle et al. | 607/101 |

* cited by examiner

Primary Examiner—Linda C. M. Dvorak
Assistant Examiner—David Ruddy
(74) Attorney, Agent, or Firm—Michael A. Glenn

(57) ABSTRACT

The invention provides a system and method for achieving the cosmetically beneficial effects of shrinking collagen tissue in the dermis in an effective, non-invasive manner, which leaves the outer layer of skin intact and undamaged. One embodiment of the invention provides electromagnetic energy to the skin of a patient. The device includes a carrier and an array of electrodes on the carrier. A microporous pad on the carrier overlies the array of electrodes, forming an interior chamber to contain an electrically conductive material. The microporous pad is adapted to contact a patient's skin and ionically transport the applied electromagnetic energy to ohmically heat dermal tissue beneath the epidermal skin region. The shape of the carrier may differ to match different skin topographies and the electrodes may be sized to extend into tissue to heat a dermal skin region.

10 Claims, 15 Drawing Sheets

SYSTEMS AND METHODS FOR SHRINKING COLLAGEN IN THE DERMIS

RELATED APPLICATION

This application is a continuation in part of copending U.S. Application Ser. No. 08/637,095, filed Apr. 29, 1996, entitled "Method and Apparatus for Controlled Contraction of Soft Tissue," which is a continuation of application Ser. No. 08/389,924, filed Feb. 16, 1995 (now U.S. Pat. No. 5,569,242), which is a continuation of application Ser. No. 08/238,862, filed May 6, 1994 (now U.S. Pat. No. 5,458,596).

FIELD OF THE INVENTION

In a general sense, the invention is directed to systems and methods for treating cosmetic conditions in the human body. In a more particular sense, the invention is directed to systems and methods for treating cosmetic conditions affecting the skin of the face and neck, as evidenced by the appearance of lines and wrinkles in the face, or neck, or both.

BACKGROUND OF THE INVENTION

The skin is the principal seat of the sense of touch. The skin also provides protection against the physical forces of the environment, such as heat, cold, sun rays, friction, pressure, and chemicals.

Exposure of the skin to these environmental forces can, over time, cause the skin to sag or wrinkle. Hyperfunctional nervous disorders and normal contraction of facial and neck muscles, e.g. by frowning or squinting, can also over time form furrows or bands in the face and neck region. These and other effects of the normal aging process can present an aesthetically unpleasing cosmetic appearance.

Accordingly, there is a large demand for systems and methods which serve to "tighten" the skin to remove sags and wrinkles in the face and neck.

One prior method surgically resurfaces facial skin by ablating the outer layer of the skin (from 200 μm to 600 μm), using laser or chemicals. In time, a new skin surface develops. The laser and chemicals used to resurface the skin also irritate or heat collagen tissue, which is widely present in the dermis. When irritated or heated in prescribed ways, the collagen tissue partially dissociates and, in doing so, shrinks. The shrinkage of collagen also leads to a desirable "tightened" look. Still, laser or chemical resurfacing leads to prolonged redness of the skin, infection risk, increased or decreased pigmentation, and scarring.

Lax et al. U.S. Pat. No. 5,458,596 describes the use of radio frequency energy to shrink collagen tissue. This cosmetically beneficial effect can be achieved in facial and neck areas of the body in a minimally intrusive manner, without requiring the surgical removal of the outer layers of skin and the attendant problems just listed.

SUMMARY OF THE INVENTION

The invention provides improved systems and methods of systems and methods of achieving the cosmetically beneficial effects of shrinking collagen tissue in the dermis in an effective, non-invasive manner, which leaves the outer layer of skin intact and undamaged.

One aspect of the invention provides systems and methods for applying electromagnetic energy to skin. The systems and methods include a carrier and an array of electrodes on the carrier, which are connectable to a source of electromagnetic energy to apply the electromagnetic energy. According to this aspect of the invention, a microporous pad on the carrier overlays the array of electrodes, forming an interior chamber to contain an electrically conductive material. The microporous pad is adapted, in use, to contact an epidermal skin region and ionically transport the applied electromagnetic energy to ohmically heat dermal tissue beneath the epidermal skin region.

In one embodiment, the shape of the carrier can differ to match different skin region topographies.

Another aspect of the invention provides systems and methods for applying electromagnetic energy to skin, in which the array of electrodes on the carrier are sized so that, while the carrier contacts an epidermal skin region, the electrodes extend into tissue beneath the epidermal skin region to ohmically heat dermal tissue.

In one embodiment, the electrodes are sized to extend into dermal tissue. In another embodiment, the electrodes are sized to extend into subdermal tissue.

In one embodiment, the shape of the carrier can differ to match different skin region topographies.

Another aspect of the invention provides systems and methods for applying electromagnetic energy to a facelift flap. The systems and methods include a carrier and at least one electrode on the carrier connectable to a source of electromagnetic energy to apply the electromagnetic energy. The electrode is sized so that, while the carrier contacts a backside of the flap, the electrode ohmically heats the dermal tissue.

In one embodiment, the electrode, in use, rests on a surface on the backside of the flap.

In another embodiment, the electrode is sized to extend into dermal tissue within the flap.

Another aspect of the invention provides a family of devices for applying electromagnetic energy to skin. Each device comprising a carrier having a shape and an array of electrodes on the carrier connectable to a source of electromagnetic energy to apply the electromagnetic energy. According to this aspect of the invention, the shapes of the carriers differ to match different skin region topographies.

In one embodiment, the carrier is adapted, in use, to contact epidermal tissue. In this embodiment, the electrodes are sized to extend into tissue beneath the epidermal tissue. The electrodes can be sized to extend into dermal tissue. Alternatively, the electrodes are sized to extend into subdermal tissue.

Features and advantages of the inventions are set forth in the following Description and Drawings, as well as in the appended Claims.

Figure 2:
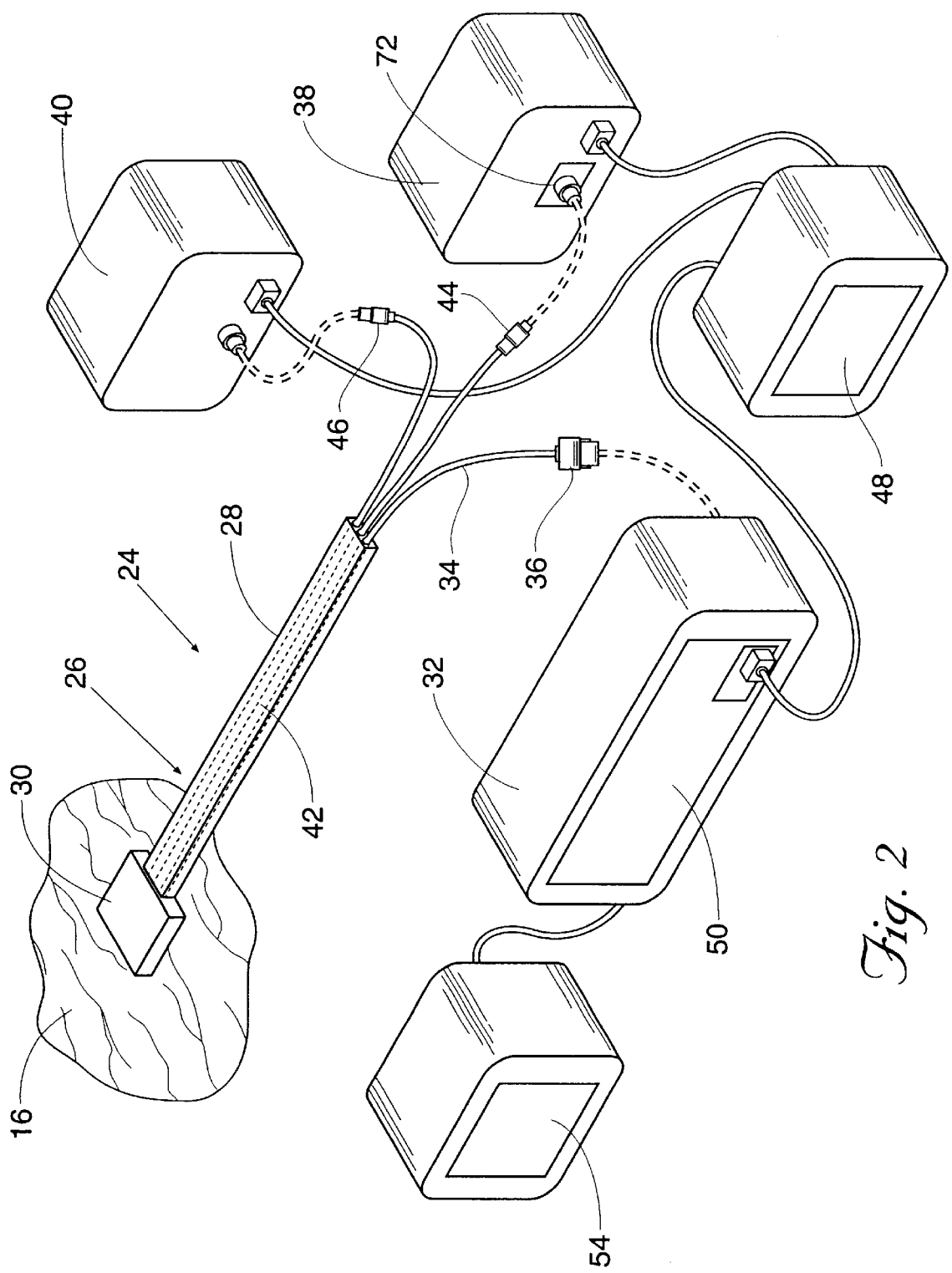
FIG. 2 is a schematic view of a system that, in use, heats collagen tissue in the dermis for the purpose of treating cosmetic conditions affecting the skin.
Figure 6:
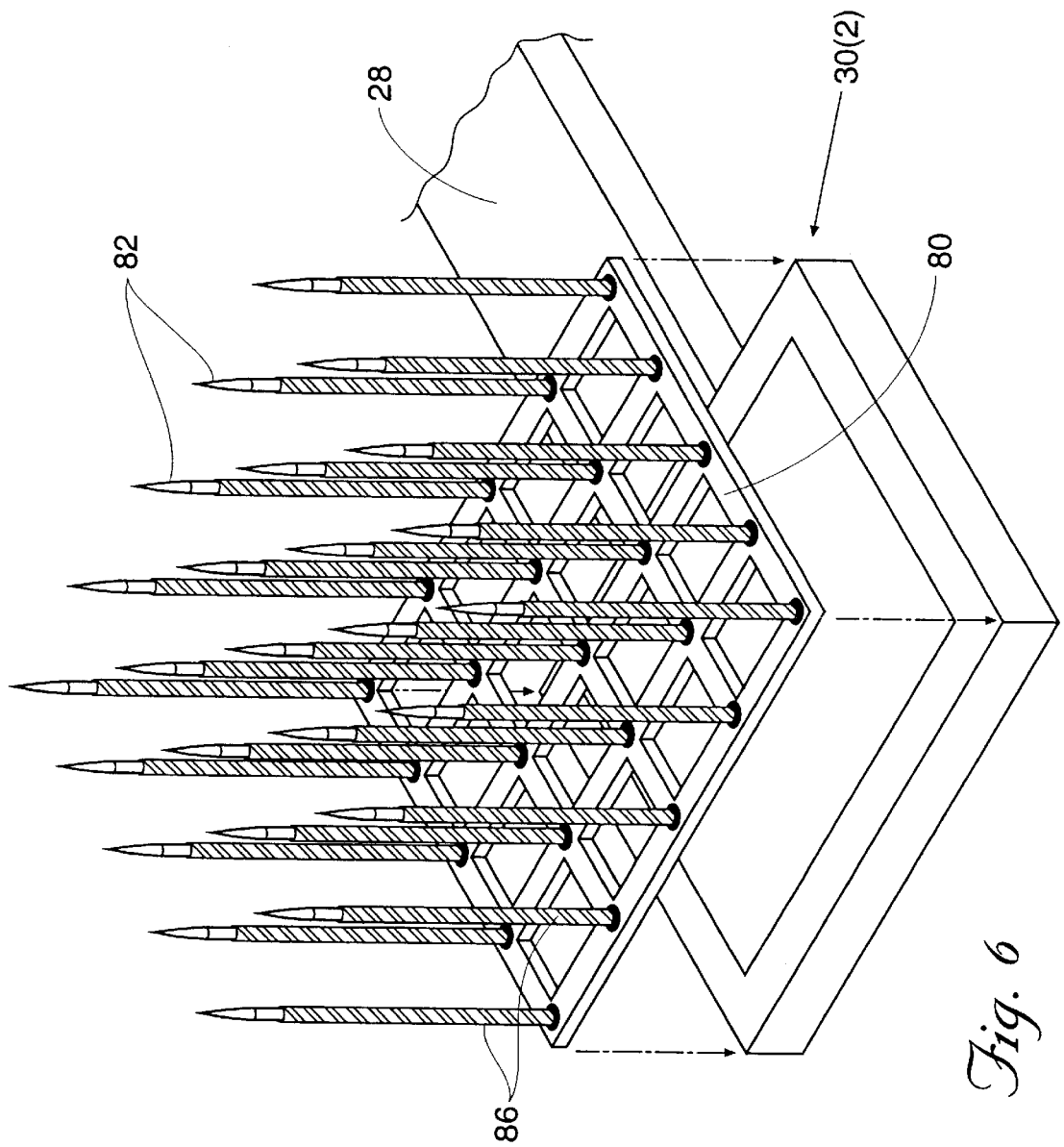
Figure 7:
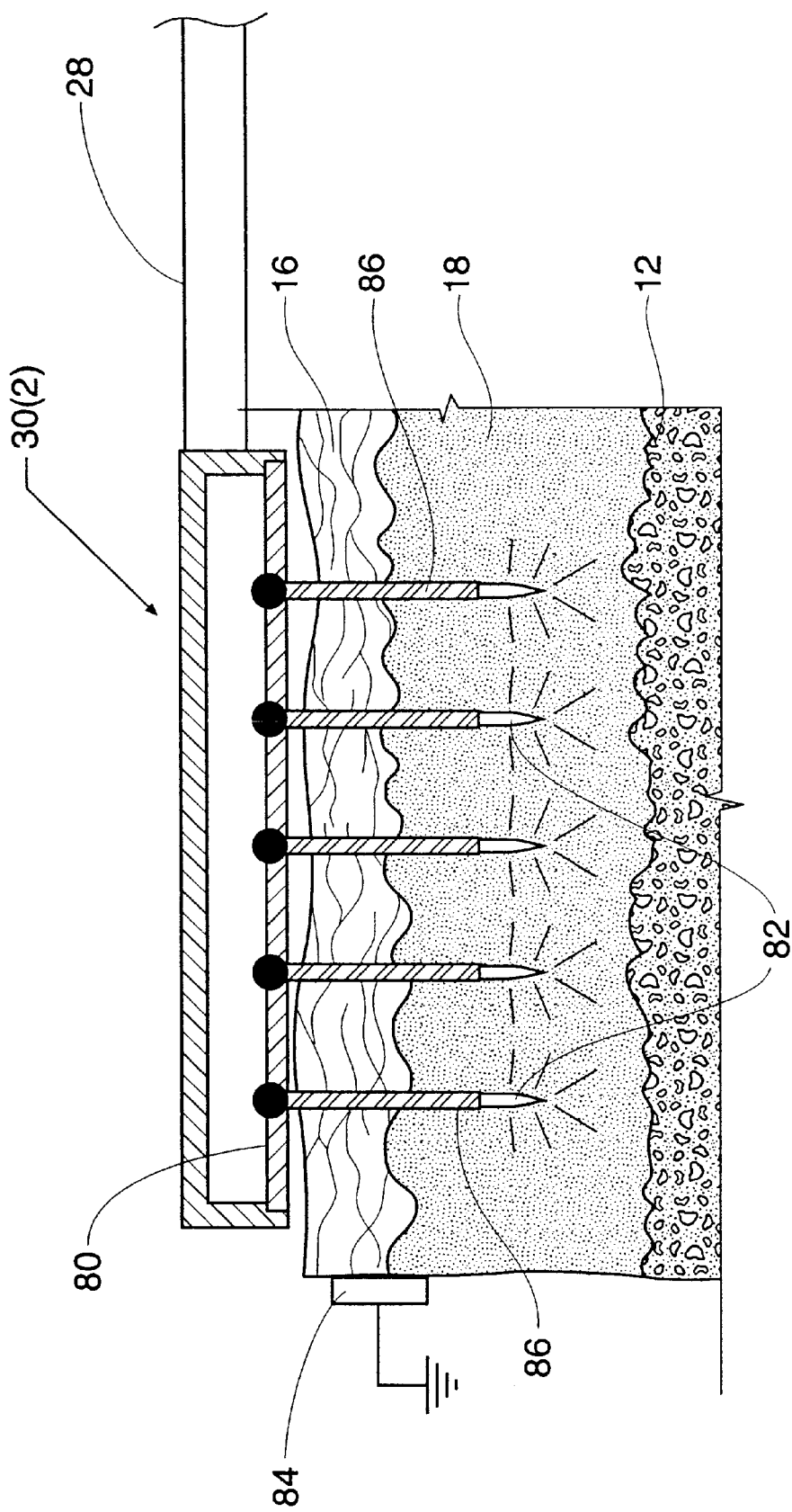
Figure 8:
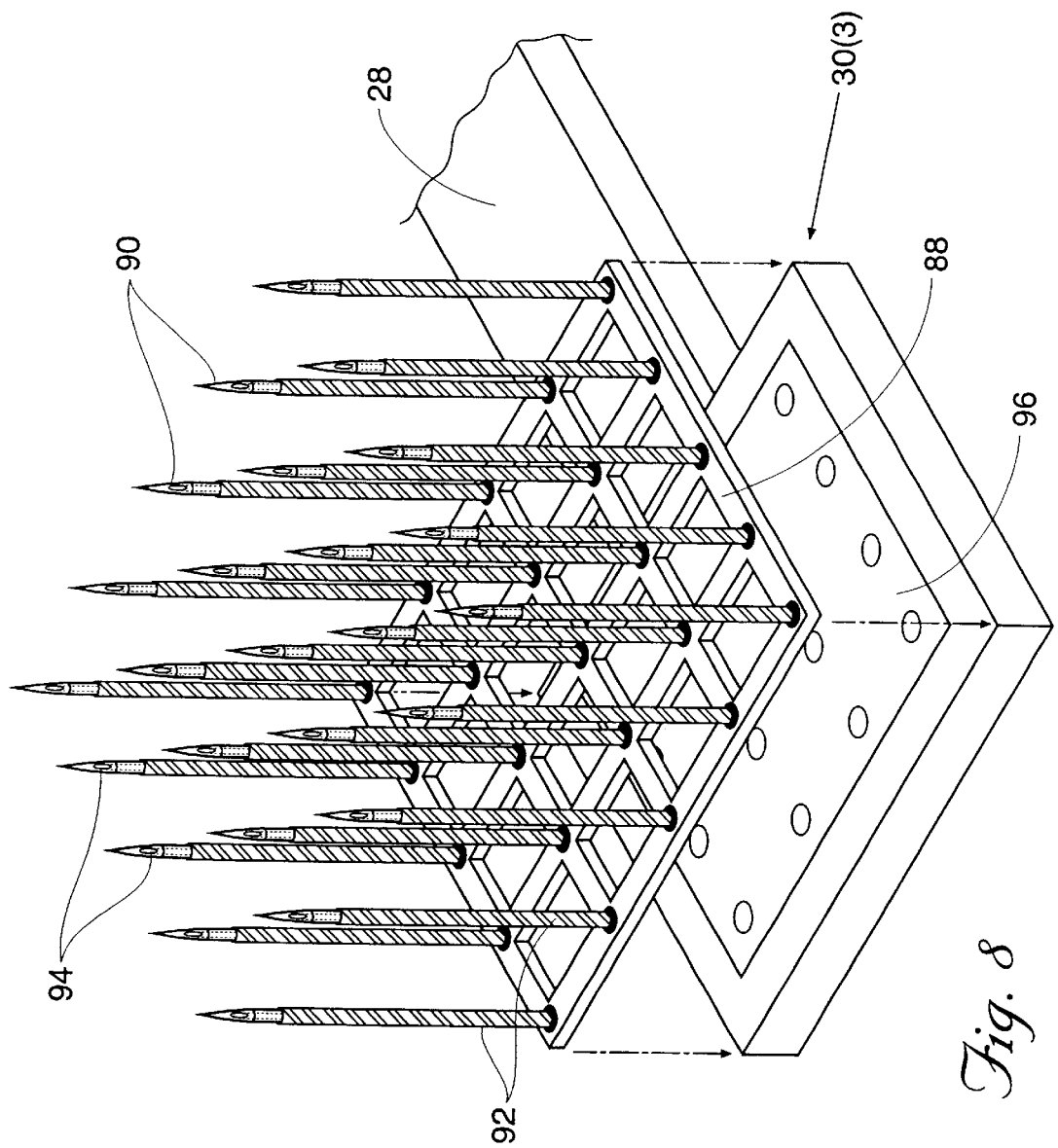
Figure 9:
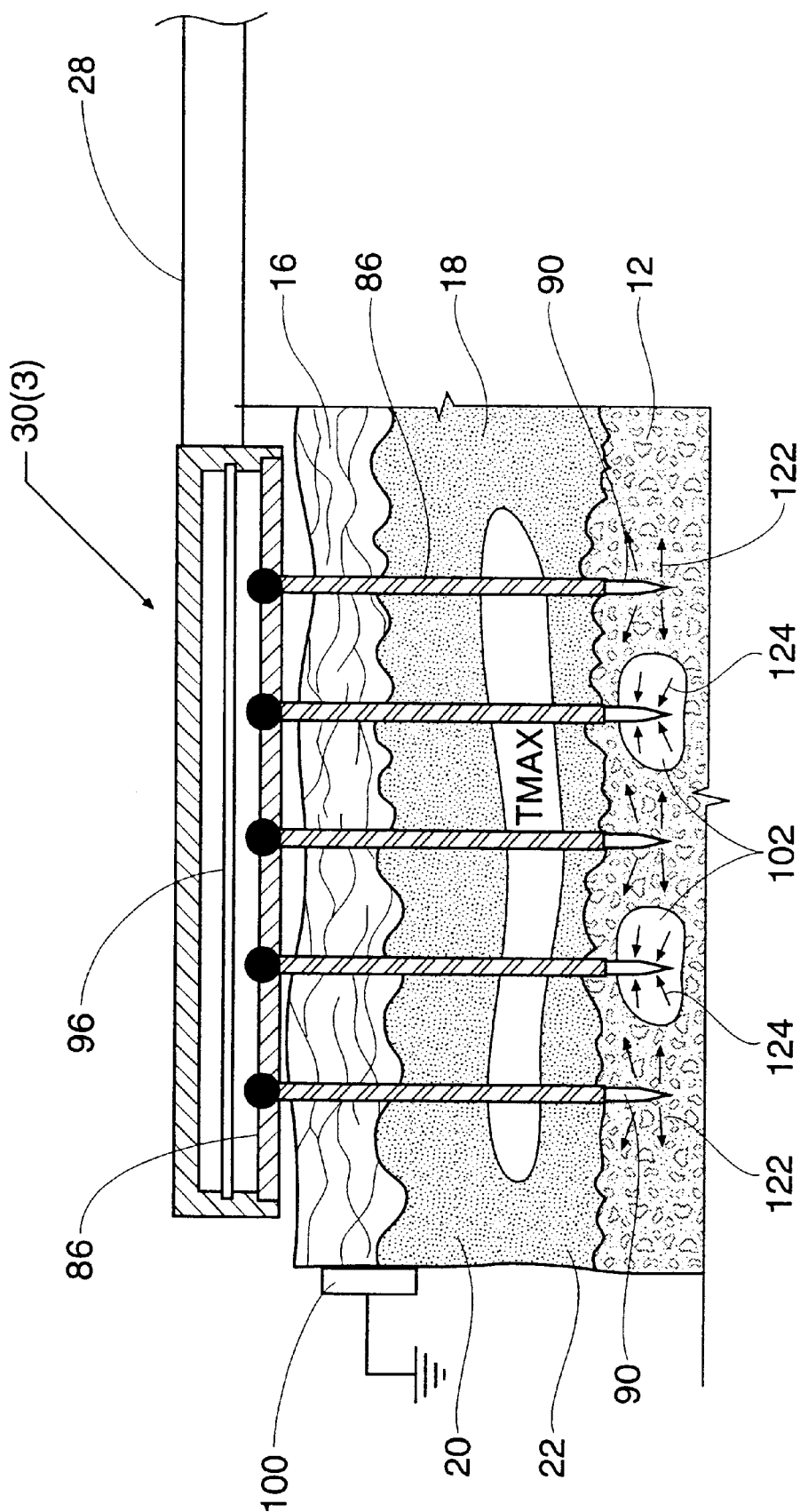
Figure 10:
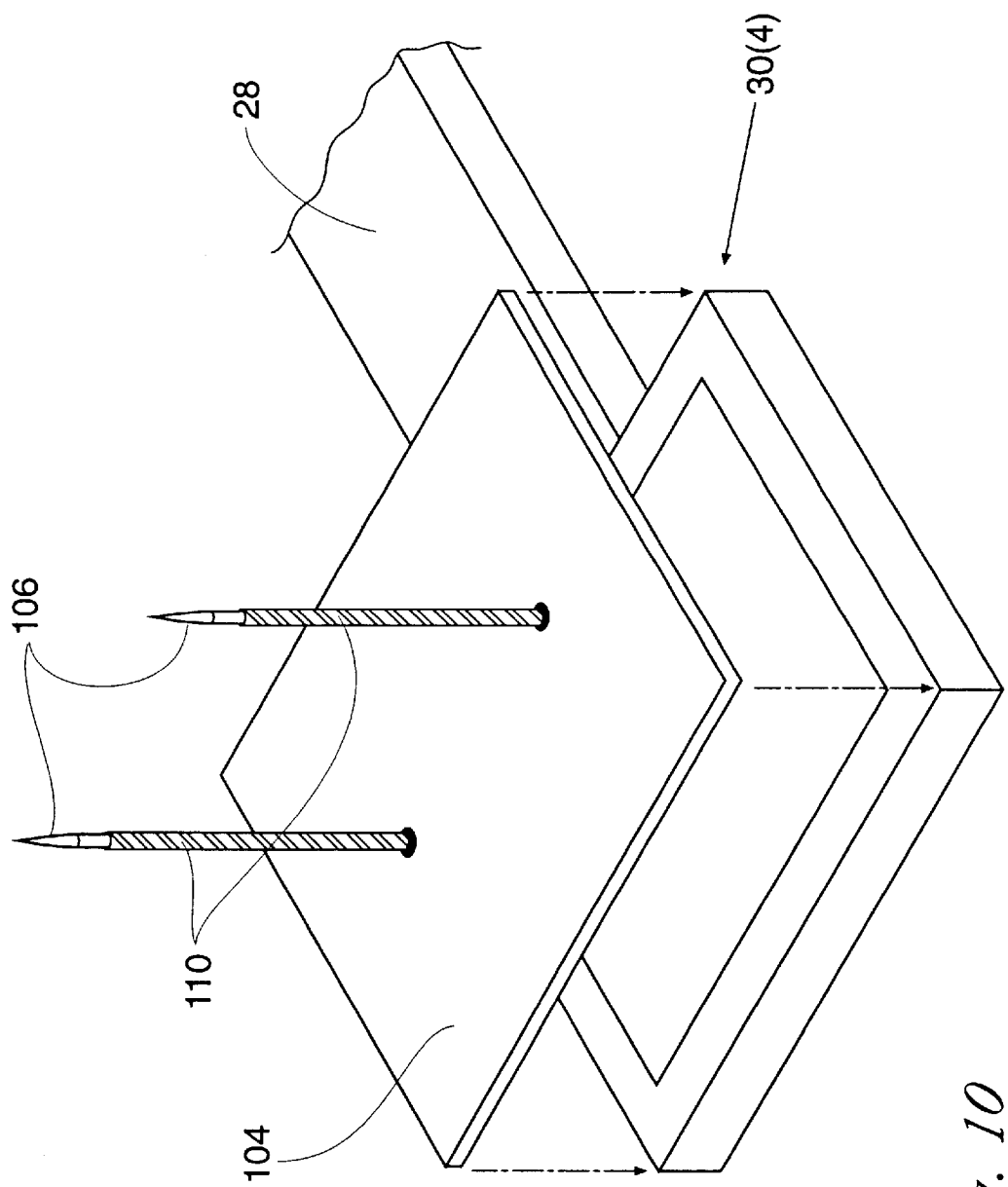

3, specially shaped to match the topography of a skin region under the eye, below the ear, under the chin, around the lips, and on the forehead above the eyebrows;

FIG. 6 is an exploded perspective view of another category of an energy applicator, usable in association with the system shown in FIG. 2, to transmit energy internally directly into the dermis;

FIG. 7 is a side section view of the energy applicator shown in FIG. 6 in use to heat collagen tissue in the dermis;

FIG. 8 is an exploded perspective view, with portions in section, of another category of an energy applicator, usable in association with the system shown in FIG. 2, to transmit energy into the dermis internally through subcutaneous tissue;

FIG. 9 is a side section view of the energy applicator shown in FIG. 8 in use to heat collagen tissue in the dermis;

FIG. 10 is an exploded, perspective view of another category of an energy applicator, usable in association with the system shown in FIG. 2, to transmit energy into the dermis from the backside of a surgically created facelift flap.

Figure 3:
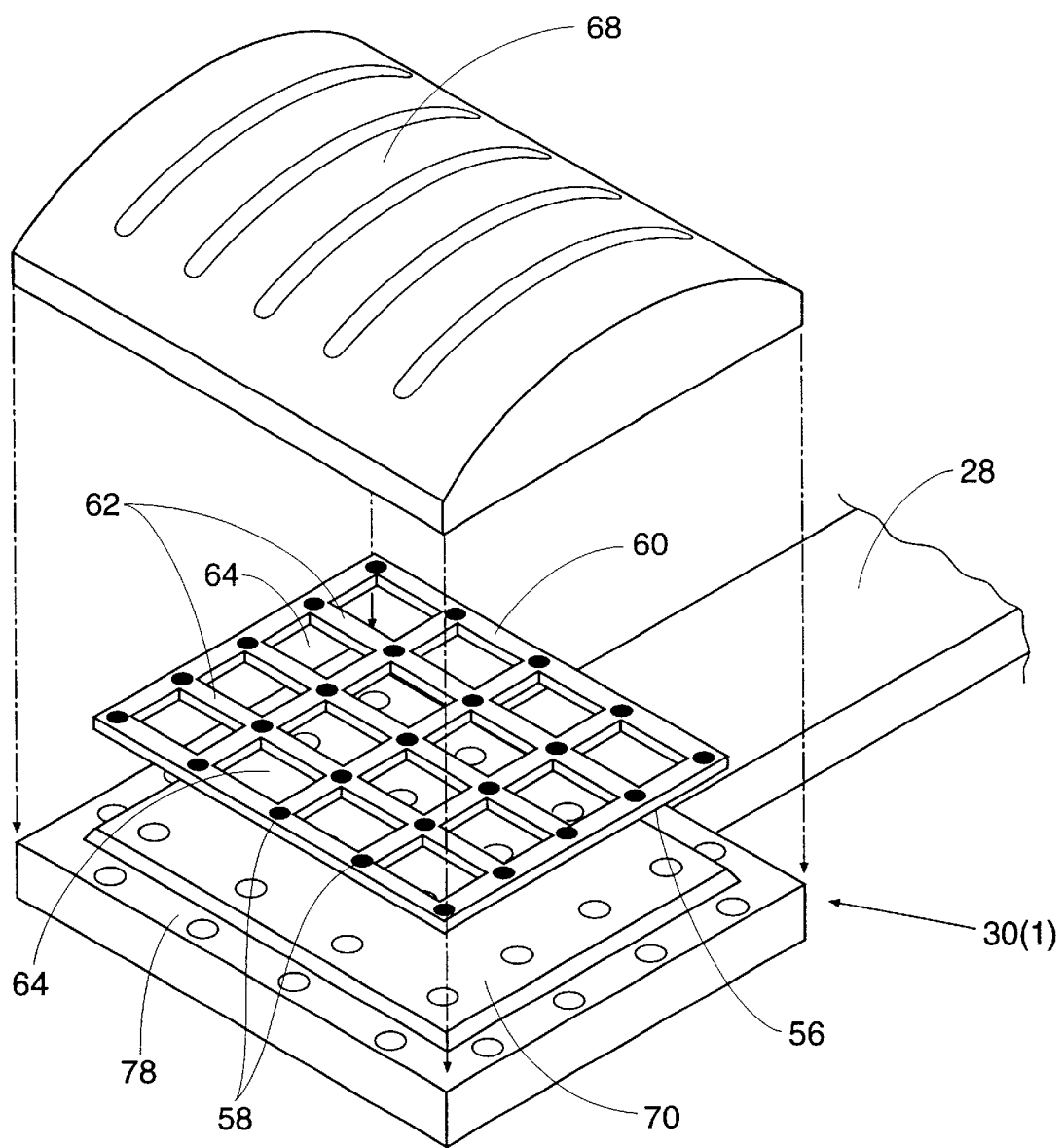
FIG. 3 is an exploded perspective view of one category of an energy applicator, usable in association with the system shown in FIG. 2, to transmit energy into the dermis externally through the epidermis.
Figure 11:
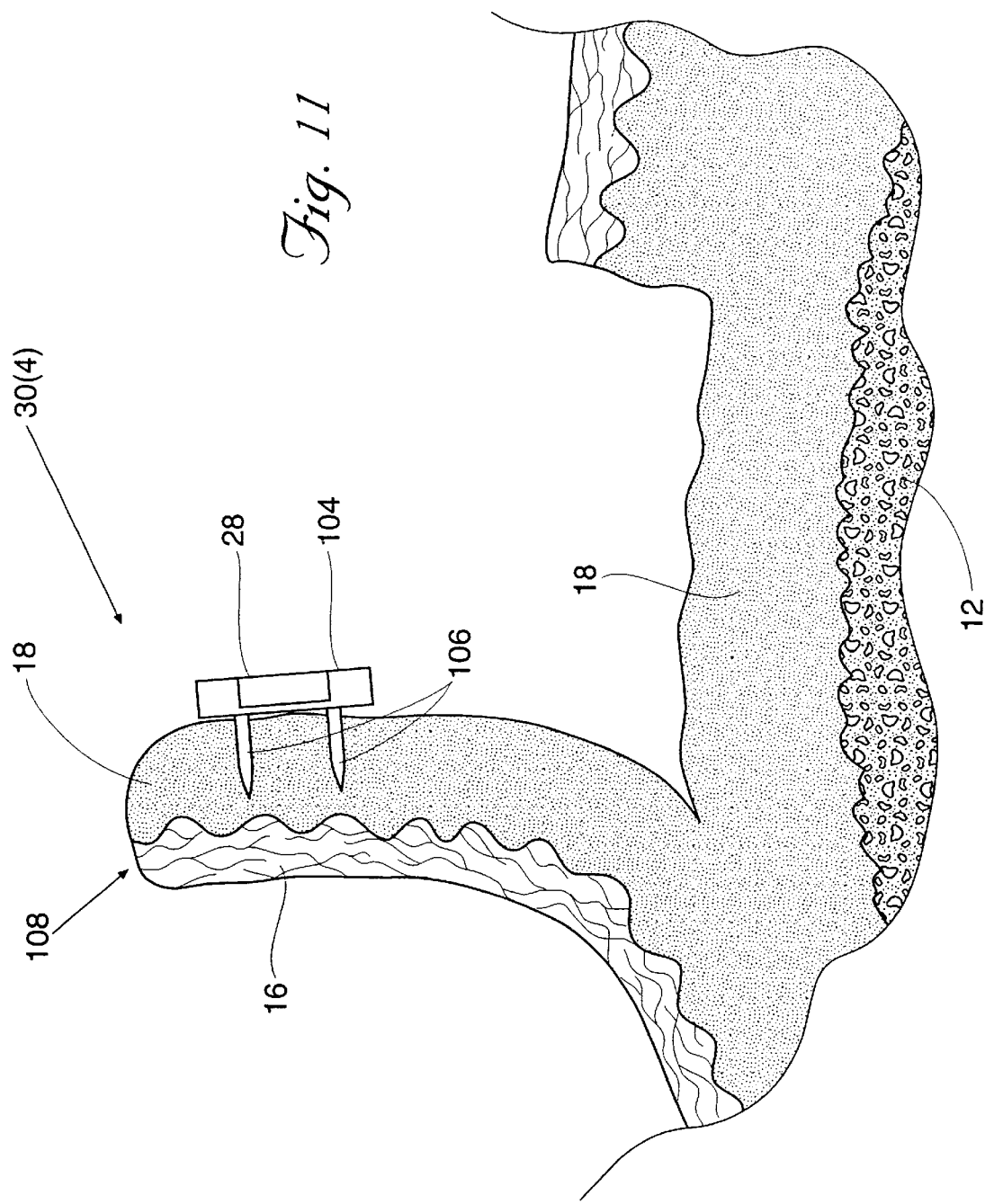
Figure 12:
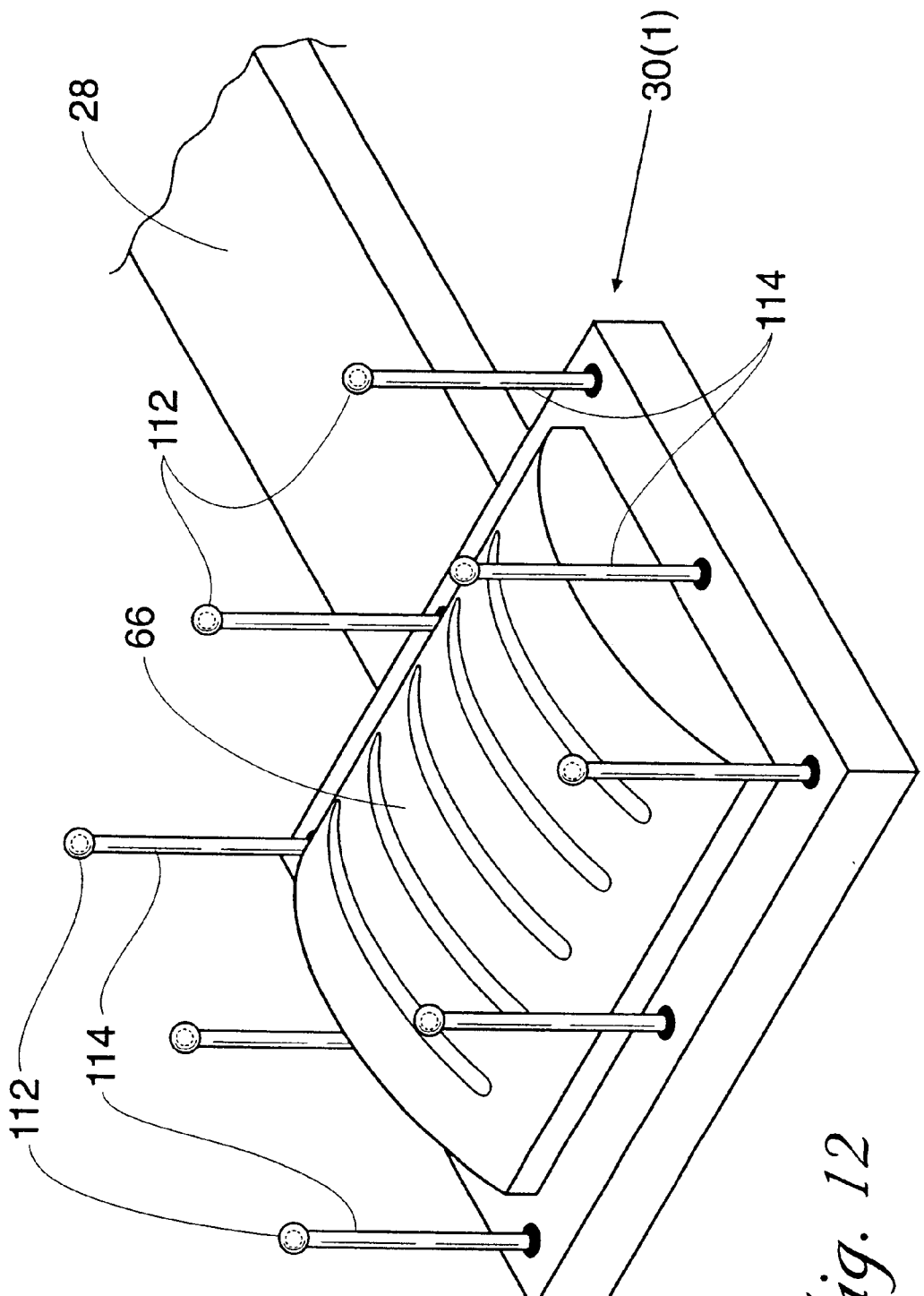
Figure 13:
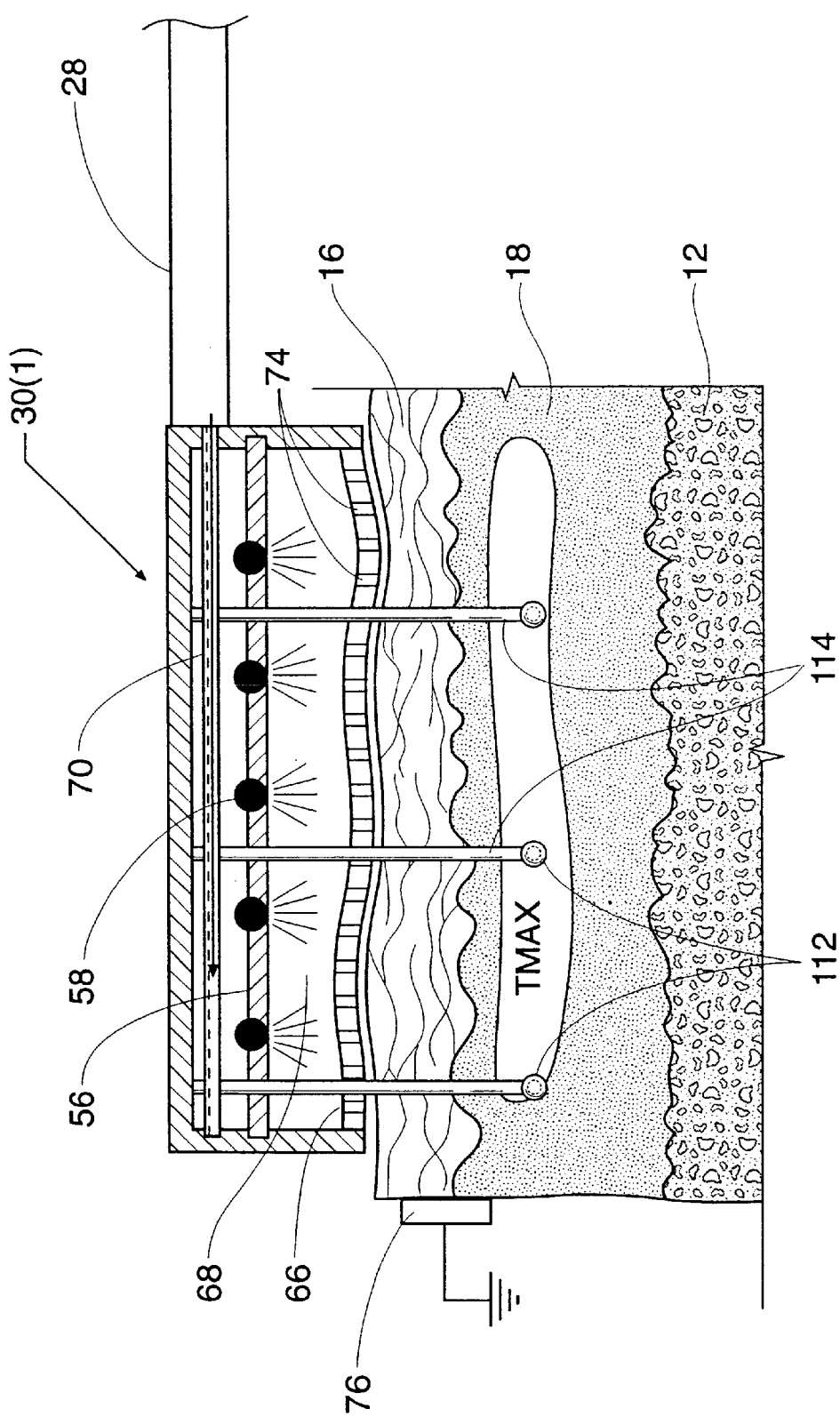
Figure 14:
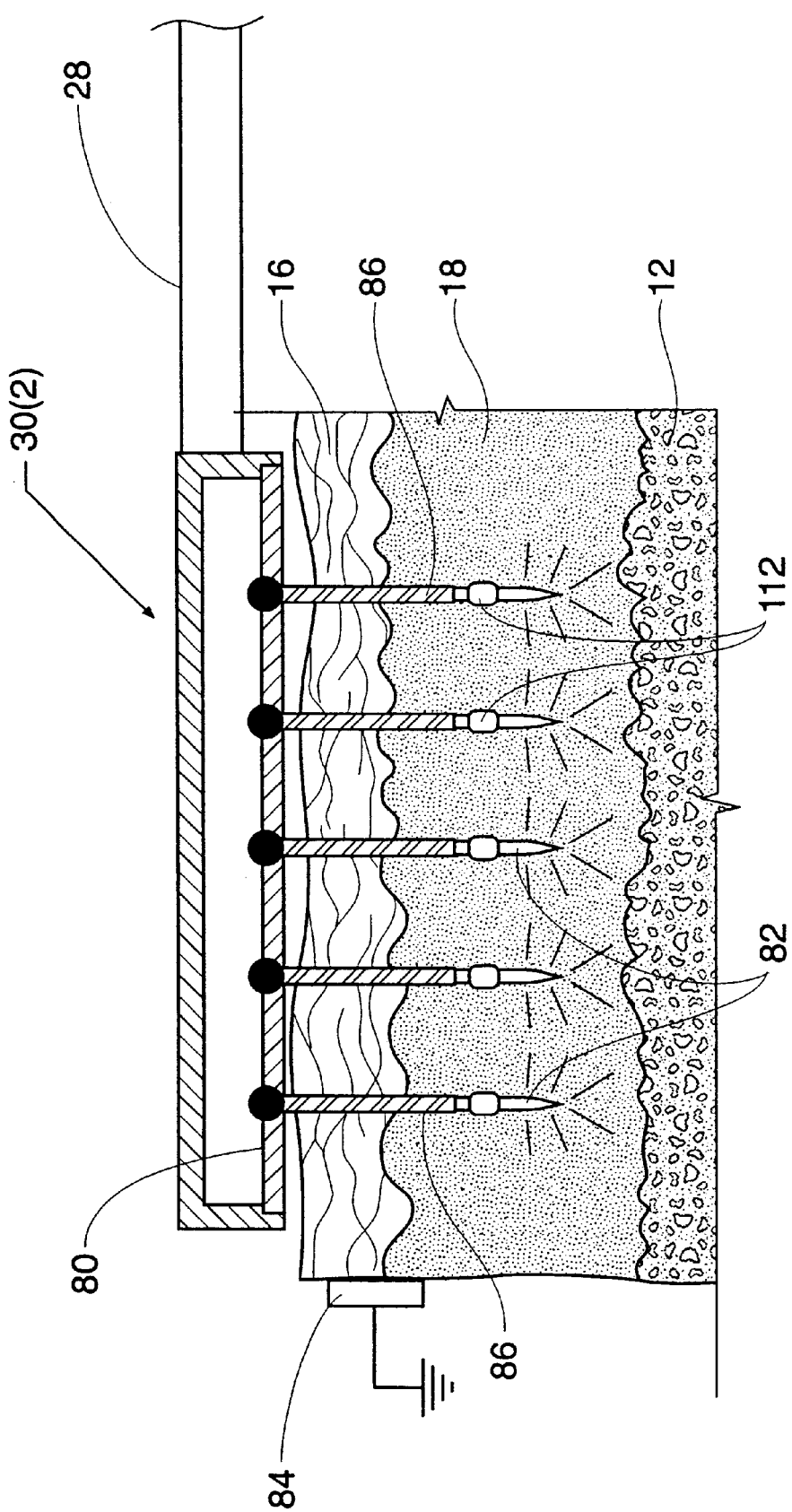
Figure 15:
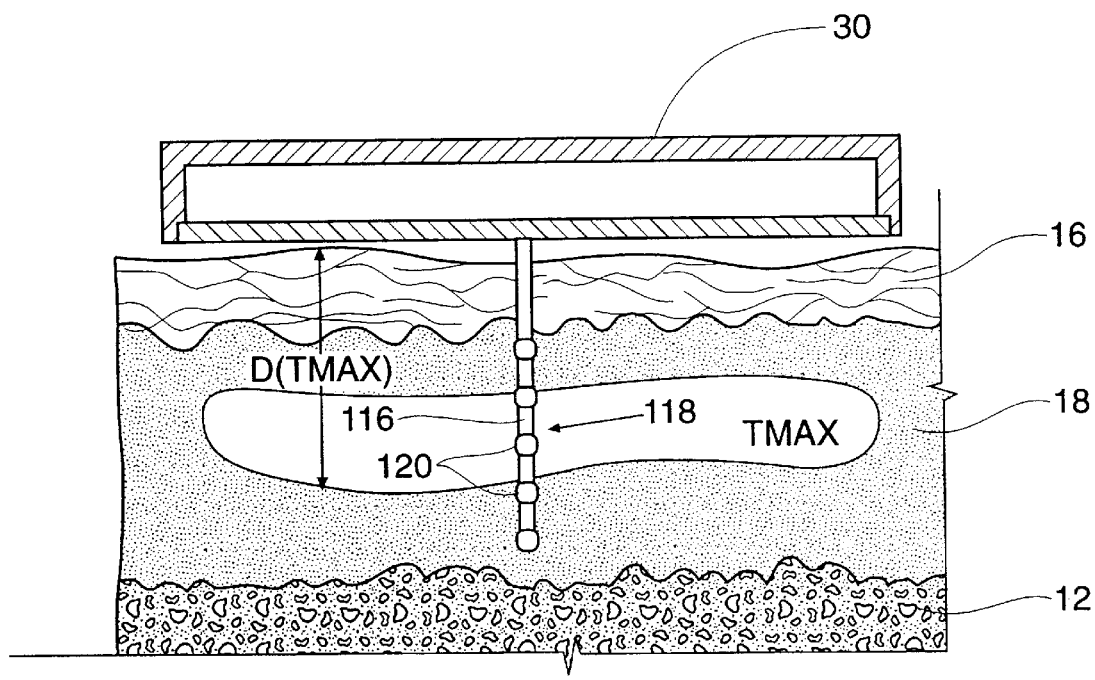

FIG. 11 is a side section view of the energy applicator shown in FIG. 10 in use to heat collagen tissue in the dermis from the backside of a facelift flap;

FIG. 12 is a perspective view of an energy applicator of the type shown in FIG. 3, with associated probes for sensing temperature in the dermis;

FIG. 13 is a side section view of an energy applicator shown in FIG. 3, with the sensors deployed in the dermis to sense temperature conditions;

FIG. 14 is a side section view of an energy applicator of the type shown in FIG. 6, with associated sensors located in the dermis to sense temperature conditions; and FIG. 15 is a side section view of a penetration tissue temperature sensing probe of the type shown in FIGS. 12 to 14, with multiple sensors deployed in a stacked arrangement to sense a temperature gradient in the dermis.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

The invention provides systems and methods of treating cosmetic conditions affecting the skin. The system and methods are applicable for use throughout the body. However, the systems and methods are particularly well suited for treating cosmetic conditions in the facial or neck area of the body. For this reason, the systems and methods will be described in this context.

I. Anatomy of the Skin

Figure 1:
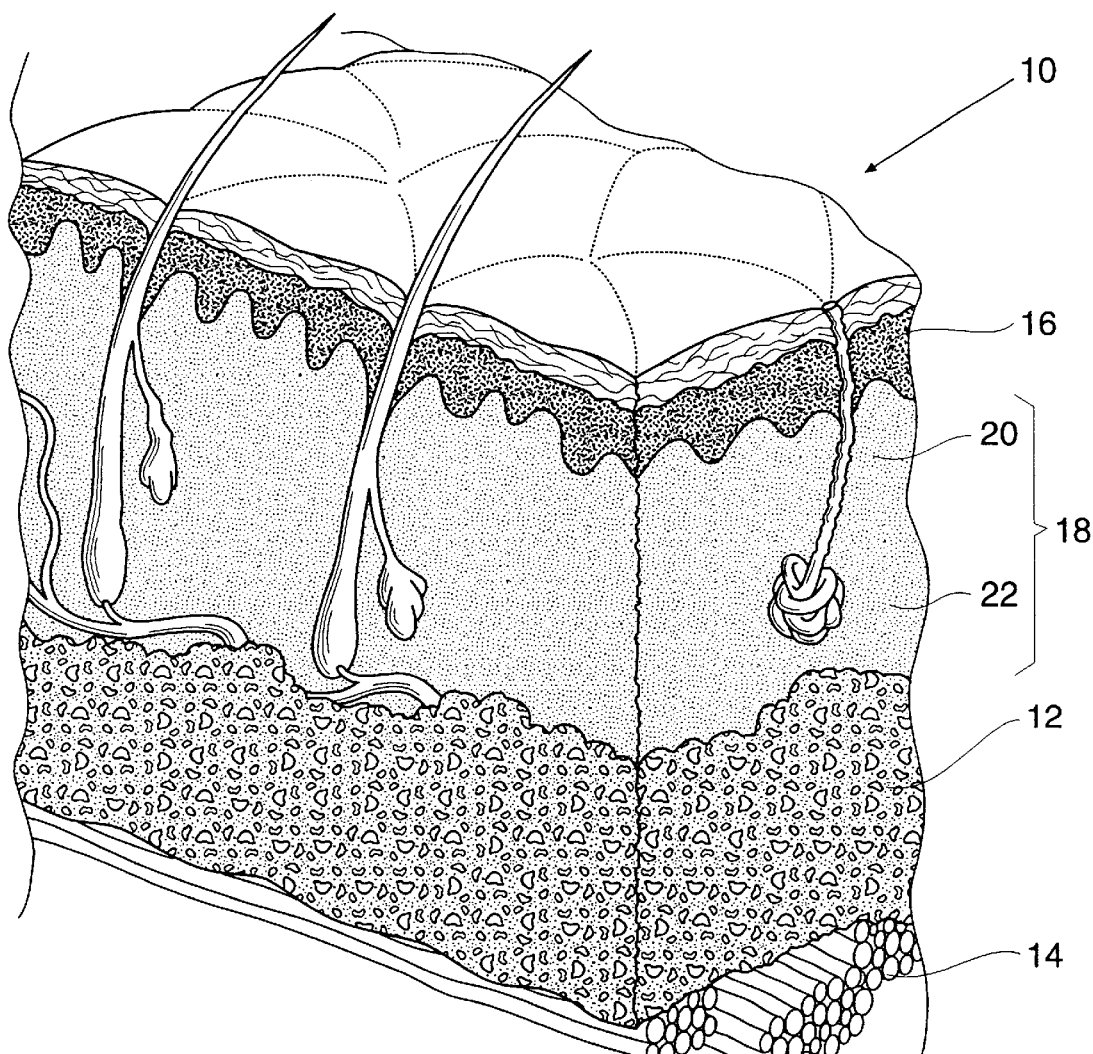
FIG. 1 is a representative side section view of skin and underlying subcutaneous tissue.

As FIG. 1 shows, the skin 10 overlies and protects subcutaneous tissue 12 and muscle tissue 14 of the body. In the face and neck areas, the skin 10 measures about 2mm in cross section.

The skin 10 includes an external, non-vascular covering of epithelial cells, called the epidermis 16. In the face and neck regions, the epidermis measures about 100 µm in cross section.

The skin 10 also includes a layer of vascular tissue, named the dermis 18. In the face and neck regions, the dermis 18 measures about 1900 µm in cross section.

The dermis 18 is tough, flexible, and highly elastic. It is divided into a papillary (upper) layer 20 and a reticular (lower) layer 22. The most numerous fibers in the papillary and reticular layers 20 and 22 are collagen fibers, which in large part account for the strength and physical properties of the dermis 18. Hair bulbs, sweat ducts, and other glands also occupy the reticular layer 22.

The fibrous structure of collagen tissue is observed to dissociate and contract along its length when heated to a defined temperature condition, i.e., about 65° C. The contraction of collagen tissue causes the dermis 18 to reduce in size, which has an observable tightening effect. As collagen contacts, wrinkles and sag lines in the skin are ameliorated. As a result, the outward cosmetic appearance of the skin 10 improves.

The temperature conditions conducive to the beneficial results of collagen shrinkage lay well above the temperature conditions at which irreversible thermal damage to epithelial cells begins to occur, i.e., above about 47° C.

II. Systems for Renovating the Dermis

A. System Overview

FIG. 2 shows a system 24 for renovating and reconstituting the dermis. The system 24 applies energy to the dermis to elevate and maintain its temperature at a predetermined temperature condition, at or about 65° C., without increasing the temperature of the epidermis beyond 47° C. In this way, the system applies energy to the dermis in a targeted, selective fashion, to dissociate and contract collagen tissue, while preserving and protecting epithelial cells against thermal damage.

The system 24 includes a treatment device 26. The device 26 includes a handle 28 made, e.g., from molded plastic. The handle 28 carries at its distal end a treatment energy applicator 30, which, in use, contacts the epidermis. The handle 28 is sized to be conveniently grasped like a pencil or paint brush by a physician, to thereby manipulate the applicator 30 on the epidermis 16.

The system 24 further includes a device 32 to generate treatment energy. In the illustrated embodiment, the generator 32 generates radio frequency energy, e.g., having a frequency in the range of about 400 kHz to about 10 mHz.

A cable 34 extending from the proximal end of the handle 28 terminates with an electrical connector 36. The cable 34 is electrically coupled to the applicator 30, e.g., by wires that extend through the interior of the handle 28. When connector 36 plugs into the generator 32, to convey the generated energy to the applicator 30 for transmission to the skin.

The system 24 also includes certain auxiliary processing equipment 38 and 40. In the illustrated embodiment, the processing equipment 38 comprises an external fluid delivery apparatus, and the processing equipment 40 comprises an external aspirating apparatus.

The handle 28 of the treatment device 26 includes one or more interior lumens 42. The lumens terminate in fittings 44 and 46, located at the proximal end of the handle 28. One fitting 44 connects to the fluid delivery apparatus 38, to convey processing fluid to the distal end of the handle 28 for discharge. The other fitting 46 connects to the aspirating apparatus 40, to convey aspirated material from the distal end of the handle 28 for discharge.

The system 24 also includes a controller 48. The controller 48, which preferably includes a central processing unit (CPU), is linked to the generator 32, the fluid delivery apparatus 38, and the aspirating apparatus 40. The controller 48 governs the power levels, cycles, and duration that the radio frequency energy is distributed to the applicator 30, to achieve and maintain power levels appropriate to achieve the desired treatment objectives. In tandem, the controller 48 also governs the delivery of processing fluid to the applicator 30 and the removal of aspirated material from the applicator 30.

The controller 48 includes an input/output (I/O) device 50. The I/O device 50 allows the physician to input control and processing variables, to enable the controller 48 to generate appropriate command signals. The I/O device 50 also receives real time processing feedback information from one or more sensors 52 associated with the applicator, for processing by the controller 48, e.g., to govern the application of energy and the delivery of processing fluid. The I/O device 50 also includes a display 54, to graphically present processing information to the physician for viewing or analysis.

B. The Treatment Device

The structure of the treatment device 26 and associated electrical energy applicator 30 can vary.

The illustrated embodiments describe and show four representative categories of energy applicators 30, as follows:

(i) a first category applicator 30(1) (shown in FIGS. 3 and 4) transmits energy into the dermis externally through the epidermis.

(ii) a second category applicator 30(2) (shown in FIGS. 6 and 7) transmits energy internally directly into the dermis.

(iii) a third category applicator 30(3) (shown in FIGS. 8 and 9) transmits energy into the dermis internally through subcutaneous tissue.

(iv) a fourth category applicator 30(4) (shown in FIGS. 10 and 11) transmits energy into the dermis from the backside of a surgically created facelift flap.

The various categories of energy applicators 30(1), 30(2), 30(3), and 30(4) will now be discussed in greater detail.

(i) EPIDERMAL ENERGY APPLICATOR

In this category, as shown in FIG. 3, the energy applicator 30(1) includes a carrier grid 56, which is mounted on the distal end of the handle 28. The carrier grid 56 is made from an electrically non-conducting material, e.g., plastic or ceramic.

The carrier grid 56 carries a pattern of multiple, spaced apart electrodes 58. Each electrode 58 comprises a discrete transmission source of radio frequency energy. The electrodes 58 can be made, e.g., from stainless steel, platinum, and other noble metals, or combinations thereof. The electrodes 58 may be fastened to the grid by various means, e.g., by adhesives, by painting, or by other coating or deposition techniques.

In the illustrated embodiment, the carrier grid 56 is formed by an outside frame 60 with crossing interior spacers 62. Together, the frame 60 and spacers 62 define an open lattice of cells 64. In the illustrated embodiment, the grid 56 defines sixteen cells 64. It should be appreciated that the cells 64 could number more or less than sixteen.

In the illustrated embodiment, the electrodes 58 are located on the grid 56 at the four corners of each cell 64. This arrangement provides a symmetric pattern of twenty-five electrodes 58 on the grid 56. Still, it should be appreciated that the electrodes 58 could be arranged in other symmetric or nonsymmetric patterns in the grid.

Figure 4:
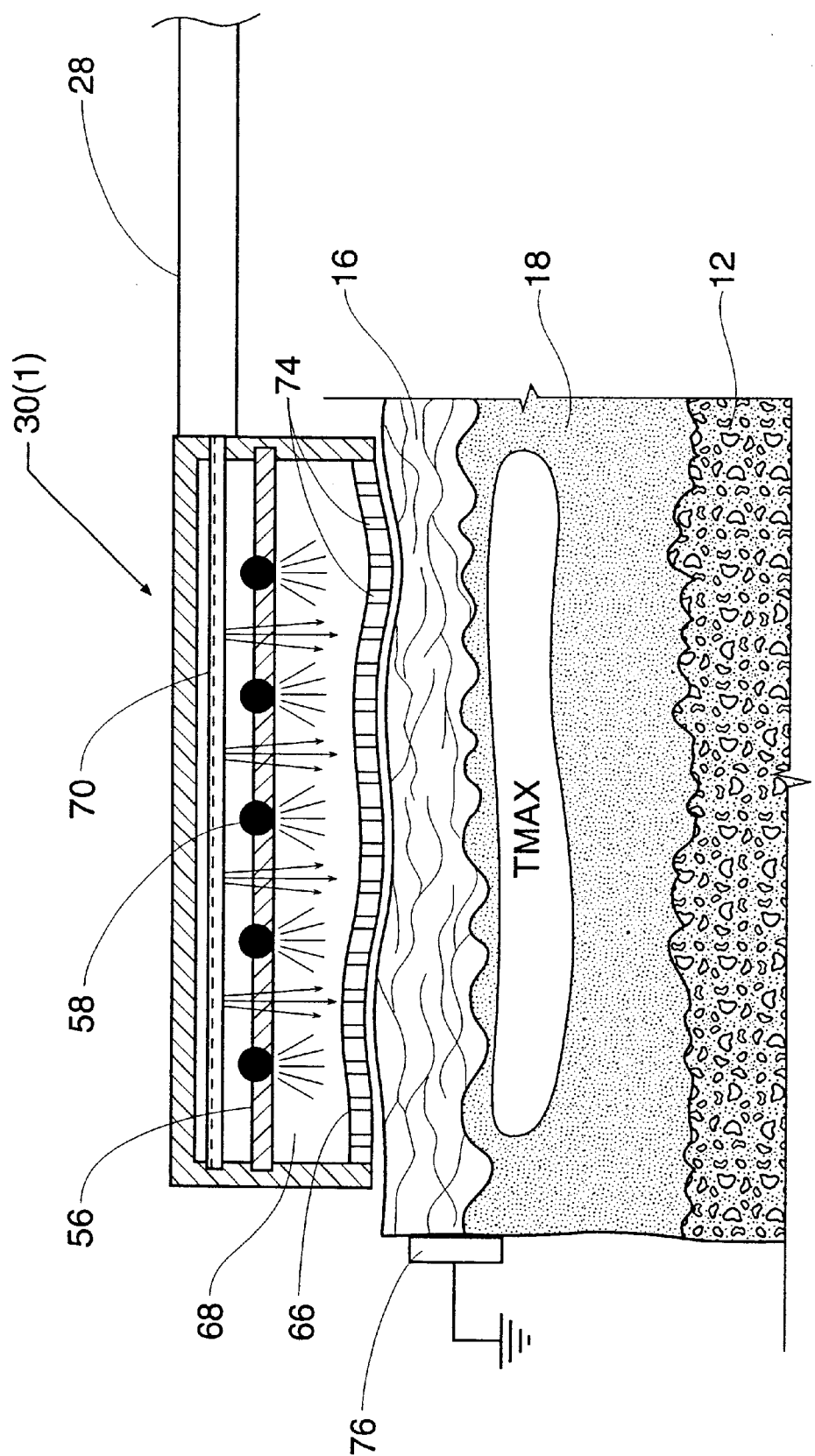
FIG. 4 is a side section view of the energy applicator shown in FIG. 3 in use to heat collagen tissue in the dermis.

In the embodiment shown in FIG. 3, the energy applicator 30(1) includes an external pad 66, which is attached peripherally about the carrier grid 56. The pad 66 is made from a resilient microporous membrane. As FIG. 4 shows, the pad 66, in use, makes surface contact with the epidermis 16. The resilience of the pad 66 makes it well suited to conform to a variable surface topography of the epidermis 16.

The attachment of the pad about the carrier grid 56 creates an interior chamber 68, which encloses the grid 56. The applicator 30(1) further includes a fluid manifold 70 inside the chamber 68. The fluid manifold 70 communicates with the fluid delivery apparatus 38, via the handle lumens 42. The manifold 70 uniformly introduces processing fluid through the grid 56 and into the interior chamber 68.

In this arrangement, the processing fluid comprises an electrically conductive liquid, such as saline (about 0.9% to 3.0%). The apparatus 38 includes a pump 72 to convey the electrically conductive liquid through the manifold 70 at a prescribed rate.

The flow of the electrically conductive liquid into the through the grid 56 and into interior chamber 68 contacts the interior surface of the microporous membrane of the pad 66. As FIG. 4 shows, the microporous membrane of the pad 66 has pores 74 sized to permit passage of the electrically conductive fluid in the chamber 68 through the membrane and into contact with the epidermis 16 the membrane contacts.

The diffusion of electrically conductive liquid through the membrane pores 74 serves two purposes. First, it creates conductive cooling at the interface between the membrane pad 66 and the epidermis 16. Second, it serves to ionically transport radio frequency energy transmitted by the grid electrodes 58 through the membrane pores 74, for return (in a unipolar arrangement) through exterior patch electrode 76 coupled to patient ground.

The ionically conducted radio frequency energy transported through the membrane pore 74 will, in turn, cause localized ohmic heating of skin tissue. The application of radio frequency energy by ionic transport to the epidermis surface, simultaneously combined with the conductive surface cooling effects that the ionic transport also provides, places the tissue region where maximum temperature conditions exist (designated TMAX in FIG. 4) at a location below the epidermis 16, into the papillary dermis 20 and, preferably, into the reticular dermis 22 as well.

The applicator 30(1) thereby makes possible selective heating of the interior dermis 18 to a maximum tissue temperature TMAX of about 65° C., while maintaining the temperature of the epidermis 16 at or about 20° C. to 30° C., thereby avoiding thermal damage to the epidermis 16.

Alternatively, an electrically conductive jelly can occupy the interior chamber 68. The jelly causes ionic transport of radio frequency energy through the membrane pores 74. In this arrangement, a manifold 78 distributes fluid about the periphery of the pad 66, but not into the chamber 68 itself, to nevertheless cause convective surface cooling effects. In this arrangement, the fluid distributed by the manifold 78 need not be electrically conductive, but it can be to provide uniform distribution of the radio frequency energy at the pad 66.

In use, the physician places the pad 66 upon a targeted region of tissue. The controller 48 governs the application of radio frequency energy to the electrodes 58 in concert with the delivery of fluid to the manifold 70 (or 78), to control the desired epidermal and dermal tissue temperature conditions. The controller 48 can also govern the withdrawal of fluid from the vicinity of the pad 66 through the aspirating apparatus 40 for this purpose. The controller 48 can alter the distribution of the radio frequency energy among selected sets or subsets of one or more grid electrodes 58. In this way, the controller 48 can focus the application of radio frequency in selected patterns.

In maintaining control of the process, the controller 48 can depend upon empirically determined or modeled relationships among selected processing variables, including, e.g., tissue temperature, time, power, and fluid delivery rate, without actual temperature sensing. Preferably, however, localized tissue temperature conditions are sensed to provide direct feedback control, as will be described in greater detail later.

In the illustrated embodiment, the handle 28 and grid 56 can comprise reusable components. In this arrangement, the energy applicator pad 66 can comprise a single use component that is temporarily fastened to the handle 28 at time of use, e.g., by a conventional snap-fit, and then removed after use for disposal.

The pad 66 need not be sized to cover a targeted facial or neck region in its entirety. Instead, the physician can locate the pad 66 in contact with a localized area of epidermal tissue within a targeted region. After applying the desired amount of radio frequency energy, the physician can relocate the pad 66 to an adjacent tissue area in the targeted region and again apply radio frequency energy. The physician can repeat this successive process, until the entire targeted region has been subject to treatment by exposure to radio frequency energy.

Figure 5:
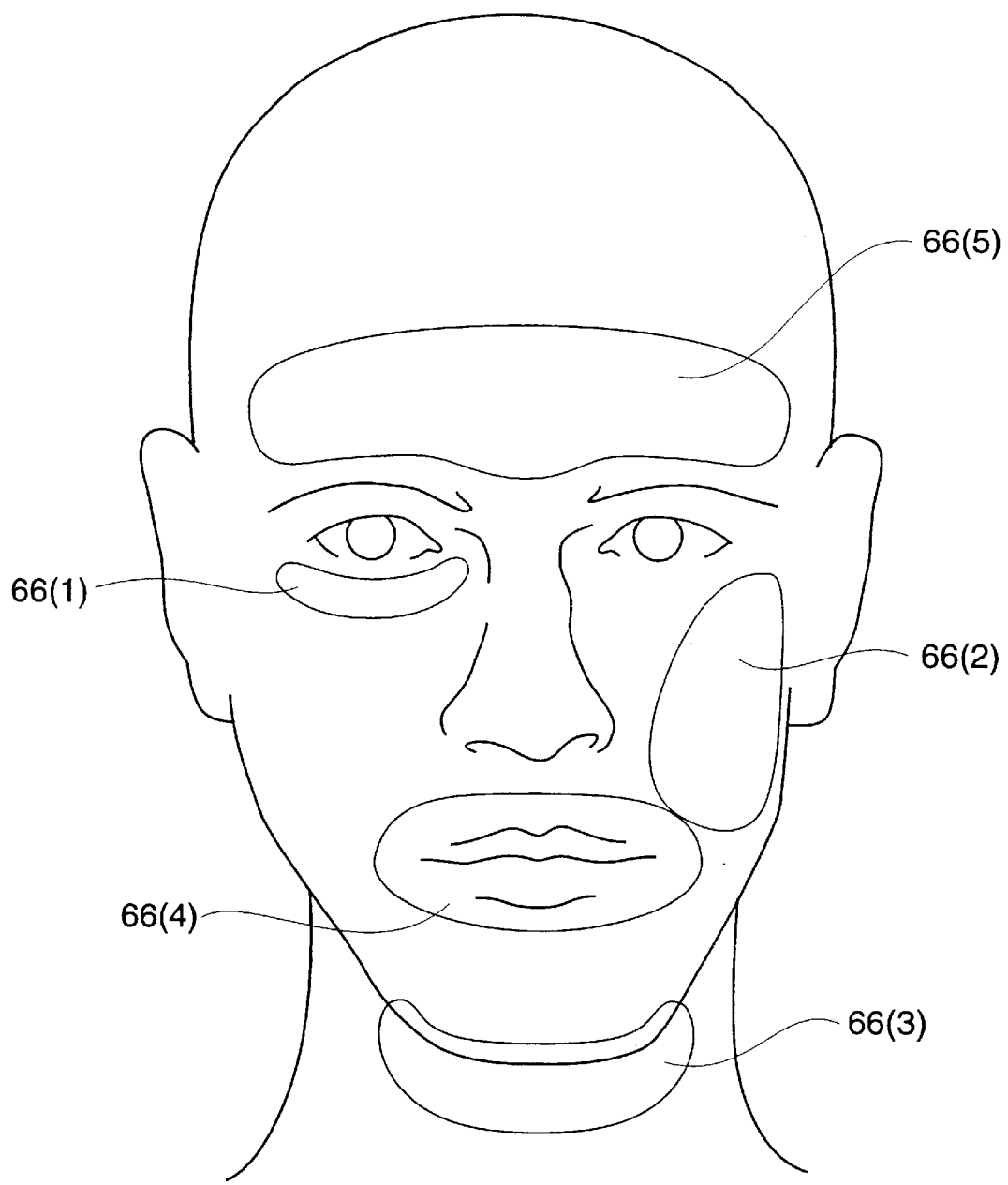
FIG. 5 is a front view of the facial and neck region showing various energy applicator, like that shown in FIG.

The energy applicator pads 66 can be specially shaped and contoured to provide different geometries, selected to match the topography of the targeted facial or neck region, e.g., under the eye (as pad 66(1) in FIG. 5 shows); or below the ear (as pad 66(2) in FIG. 5 shows); or under the chin (as pad 66(3) in FIG. 5 shows); or around the lips (as pad 66(4) in FIG. 5 shows); or on the forehead above the eyebrows (as pad 66(5) in FIG. 5 shows).

(ii) INTRADERMAL ENERGY APPLICATOR

As shown in FIG. 6, the second category of energy applicator 30(2) includes a carrier 80 on the distal end of the handle 28. The carrier 80 supports an array of spaced-apart needle electrodes 82. The electrodes 82 are metallic, being made, e.g., from stainless steel, platinum, other noble metals, or combinations thereof. Each electrode 82 comprises a discrete transmission source of radio frequency energy, which the controller 48 governs.

The carrier 80 can provide physical connections between control wires and each electrode 82, e.g., by solder or adhesive. Alternatively, the carrier 80 can have painted, coated, or otherwise deposited solid state circuitry to provide the electrical paths. The solid state circuitry can include a fuse element that interrupts electrical contact after a specified period of use, to thereby discourage reuse of the carrier 80.

In use (as FIG. 7 shows), the electrodes 82 are intended to be inserted as a unit on the carrier 80 through the epidermis 16 and into the dermis 18. After insertion, the controller 48 conditions the electrodes 82 for operation in a unipolar mode. In this mode, energy transmitted by one or more of the electrodes 82 is returned by an indifferent patch electrode 84, which is coupled to patient ground.

Alternatively, the controller 48 can condition pairs of electrodes 82 to operate in a bipolar mode, with one electrode serving to transmit radio frequency energy, and the other electrode serving as the return path.

The size and spacing of the electrodes 82 shown in FIGS. 10 and 11 are purposely set to penetrate the skin to a depth sufficient to pass entirely through the epidermis 16 and penetrate the papillary and, preferable, extend into the reticular dermis (e.g., about 200 $\mu$m to 300 $\mu$m). When used for this purpose, the electrodes 82 each possesses a total length of about 0.5 to about 3.0 mm. The electrodes are mutually spaced apart by about 0.5 mm to 10.0 mm.

An electrical insulating material 86 surrounds the proximal end of each electrode 82 by at least 0.5 mm. This leaves an exposed, non-insulated length at the distal end of about 0.5 mm to 2.5 mm. The insulating material 82 insulates the epidermis 16 and a portion of the dermis 18 from direct exposure to radio frequency energy transmitted by the exposed distal end.

The ratio between exposed and insulated regions on the electrodes 82 affects the impedance of the electrodes 82 during use. Generally speaking, the larger the exposed region is compared to the insulated region, a larger impedance value can be expected.

In use, the physician places the carrier 80 upon a desired region of tissue. The physician applies light pressure on the handle 28 to insert the needle electrodes 82 through the epidermis 16 and into the dermis 18. The controller 48 governs the application of radio frequency energy to the electrodes 82 to ohmically heat adjacent dermal tissue. The electrodes 82 can be operated individually or in groups to form defined energy application patterns. As before described, the controller 48 can depend upon the empirically determined or modeled relationships among processing variables to affect process control, with or without actual temperature sensing.

In this arrangement, the handle 28 can comprise a reusable component, and the carrier 80 with electrodes 82 can comprise a single use component, which is temporarily fastened to the distal end of the handle 28 for use and then removed after use for disposal.

As with the pad 66, the carrier 80 need not be sized to cover a targeted facial or neck region in its entirety. Instead, the physician can successive locate the carrier 80 in a localized areas within a targeted region, and apply radio frequency energy to each localized area.

Like the pad 66, the carrier 80 can also be specially shaped and contoured to provide different geometries, selected to match the topography of the targeted facial or neck region, as shown in FIG. 5.

(iii) SUBDERMAL ENERGY APPLICATOR

As shown in FIG. 8, the third category of energy applicator 30(3) includes a carrier 88 mounted on the distal end of the handle 28. Like the carrier 80 shown in FIG. 6, the carrier 88 shown in FIG. 8 holds an array of spaced-apart, metallic needle electrodes 90. Each electrode 90 comprises a discrete transmission source of radio frequency energy, which the controller 48 governs.

As before explained, the carrier 88 can provide physical connections between control wires and each electrode 90, or carry painted, coated, or otherwise deposited solid state circuitry to provide the electrical paths.

As FIG. 9 best shows, the needle electrodes 90 shown in FIG. 8 differ from the electrode 82 in FIG. 6 in that they are longer than the needle electrodes 82. The longer electrodes 90 are intended to be inserted as a unit through both the epidermis 16 and the dermis 18, and extend into the subcutaneous tissue region 12 a short distance beyond the reticular dermis 22.

For this purpose, the electrodes 90 each possesses a total length of about 3.0 mm to 10.0 mm. The electrodes 90 are mutually spaced apart by about 0.5 mm to 3.0 mm. An electrical insulating material 92 surrounds the proximal end of each electrode 90 by at least 2.0 mm. This leaves an exposed, non-insulated length at the distal end of each electrode 90 of about 3.0 mm to 4.0 mm. The insulating material 92 insulates the epidermis 16 and dermis 18 from direct exposure to radio frequency energy transmitted by the exposed distal ends of the electrodes 90.

In the illustrated embodiment, at least some, and preferably all, of the needle electrodes 90 include interior fluid passages 94 (see FIG. 8). A manifold 96 couples a select number of the passages 94 in communication with the fluid delivery apparatus 38. This way, processing fluid can be introduced through the electrodes 90 and into the subcutaneous tissue surrounding the distal ends of the electrodes 90. The manifold 96 couples other passages 94 in communication with the aspirating device 40, to evacuate material through the distal ends of the electrodes 90.

In this embodiment, the processing fluid comprises an electrically conductive liquid, such as saline. The apparatus 38 includes a pump 72 (see FIG. 1) to convey the electrically conductive liquid to the manifold 96 at a prescribed rate. The manifold 96 disperses the electrically conductive liquid through the selected passages 94.

The controller conditions the electrodes 90 to operate in a unipolar mode. Energy transmitted by one or more of the electrodes 90 is returned by an indifferent patch electrode 100, which is coupled to patient ground (see FIG. 9). At the same time, electrically conductive liquid flows through the selected passages 94 into the surrounding subcutaneous tissue region 12 (shown by arrows 122 in FIG. 9), while liquid and other material is evacuated through the other passages 94 by the aspirating device 40 (as shown by arrows 124 in FIG. 9).

The radio frequency energy transmitted by the exposed, distal ends of the electrodes 90 will cause localized ohmic heating of subcutaneous tissue. The conduction of the electrically conductive fluid ionically distributes the radio frequency energy in a uniform manner, while also providing a localized cooling effect. The cooling effect places the tissue region where maximum temperature conditions exist at a location (designated TMAX in FIG. 9) spaced from the distal ends of the electrodes 90, which includes the reticular dermis 22.

The localized heating effects will all cause fat tissue 102 in the subcutaneous tissue 12 to flow (see FIG. 9). Suction applied by the aspirating device 40 through the passages 94 can be used to evacuate flowing fat tissue from subcutaneous tissue 12 (as arrows 124 in FIG. 9 show). This provides localized liposuction effects in the subcutaneous region 12, in tandem with collagen heating effects in the dermis 18.

In use, the physician places the carrier 88 upon a desired region of tissue. The physician applies light pressure on the handle 18 to insert the needle electrodes 90 through the epidermis 16 and dermis 18 and into a subcutaneous tissue region 12. The controller 48 governs the application of radio frequency energy to the electrodes 90, which can be operated individually or in defined patterns.

The carrier 88 need not be sized to cover an entire targeted region. The physician can locate the carrier 88 in successive local areas within a targeted region, and apply radio frequency energy to each localized area. Like the pad 66, the carrier 88 can also be specially shaped and contoured to provide different geometries, selected to match the topography of the targeted facial or neck region, as shown in FIG. 5.

As before described, the controller 48 can depend upon the empirically determined or modeled relationships among processing variables to affect process control, with or without actual temperature sensing.

In this embodiment, as in the preceding embodiment, the handle 28 can comprise a reusable component, and the carrier 88 and needle electrodes 90 can comprise a single use component that is temporarily fastened to the handle 28 for use and then removed after use for disposal.

(iv) FACELIFT FLAP ENERGY APPLICATOR

As shown in FIG. 10, the fourth category of energy applicator 30(4) likewise includes a carrier 104 on the distal end of the handle 28. The carrier 104 holds a pair of bipolar metallic electrodes 106. In use, energy transmitted by one of the electrodes 106 is returned by the other electrode 106 to patient ground. Alternatively, the carrier 104 can hold an array of several needle electrodes, which are operated in either a bipolar or unipolar mode.

In use (see FIG. 11), the physician surgically creates a facelift flap 108 in the targeted tissue region. The flap 108 extends well into the dermis 18 (e.g., 200 $\mu$m to 300 $\mu$m). The physician inserts the needle electrodes 106 into the backside of the flap 108 and applies radio frequency energy.

The size and spacing of the electrodes 106 are purposely set to penetrate into the backside of the skin flap 108 to a depth sufficient to locate the distal ends of the electrodes 106 in dermal tissue.

When used for this purpose, the electrodes 106 each possesses a total length of about 3.0 mm to 8.0 mm. The electrodes 106 are mutually spaced apart by about 0.5 mm to 10.0 mm.

Alternatively, in this embodiment, the applicator 30(4) can comprise an array of surface electrodes 106 that do not penetrate the skin flap 108, but which rest on the surface of the backside of the skin flap.

As before described, the controller 48 governs application of radio frequency energy to achieve the desired tissue effects.

In this embodiment, as in preceding embodiments, the handle 28 can comprise a reusable component, and the carrier 104 and electrodes 106 can comprise a single use component that is temporarily fastened to the handle for use and then removed after use for disposal.

C. Dermal Temperature Sensing

In all of the preceding embodiments, the controller 48 preferable relies upon sensing tissue temperature conditions as a form of active process feedback control.

For this purpose, the energy applicator carries at least one sensor 112 (see FIG. 12), which senses tissue temperature conditions. In the illustrated embodiment, the at least one sensor 112 is located beneath the epidermis 16 and into the dermis 18 (see FIG. 13), to sense actual tissue temperature conditions in the dermis 18.

When used in association with the applicator pad 66 of the category (i) applicator 30(1)(as FIG. 12 shows), an array of probes 114 is arranged in a spaced-apart relationship along the periphery of the pad 66. Each probe 114 carries at least one temperature sensor 112. In use, the probes 114 extend through the epidermis 16 and into the dermis 18, as FIG. 13 shows.

When use in association with a penetrating needle electrode 82, 90, or 106, (see FIG. 14) each needle electrode 82, 90, or 106 can carry at least one temperature sensor 112. Alternatively, of course, probes could be used to carry the sensors 112, in the manner shown in FIGS. 12 and 13. In any event, the sensors 112 are located so that, in use, they are positioned in the region of the dermis 118 where radio frequency heating is targeted, as FIG. 14 shows.

In the embodiment shown in FIG. 15, a tissue penetrating probe 116 (or needle electrode, as the case may be) may support a vertically stacked array 118 of temperature sensors 120. The temperature sensors 120 are arranged at known, fixed intervals along the probe 116. The stacked sensors 120 sense a dermal tissue temperature gradient along the length of the probe 116.

The sensing of a temperature gradient within dermal tissue targeted for radio frequency heating permits the controller 48 to identify along the gradient the location of the maximum tissue temperature region TMAX. For control purposes, the controller 48 can include an algorithm that selects the maximum tissue temperature TMAX and also identifies the depth D(TMAX) at which the maximum tissue temperature occurs. By varying the power of radio frequency energy applied and the rate of surface cooling (when appropriate), the controller 48 can adjust the maximum tissue temperature TMAX to achieve the desired control point temperature, which for collagen shrinkage is 65° C. The controller 48 can also establish and maintain a control depth (D(TMAX)) at which the desired control point temperature occurs, e.g., at a skin depth of 200 $\mu$m to 300 $\mu$m (pre-set or set by the physician), to achieve optimal collagen shrinkage.

Various features of the invention are set forth in the following claims.

We claim:

1. A method for applying electromagnetic energy to skin comprising the steps of
providing a carrier, an array of electrodes on the carrier connectable to a source of electromagnetic energy to apply the electromagnetic energy, and a microporous pad on the carrier overlying the array of electrodes forming an interior chamber to contain an electrically conductive material, and
placing the microporous pad in contact with an epidermal skin region while applying the electromagnetic energy with the electrodes to tonically transport the applied electromagnetic energy through the microporous pad to ohmically heat dermal tissue beneath the epidermal skin region.

2. A method according to claim 1
further including the step of circulating the electrically conductive material in the interior chamber while applying the electromagnetic energy.

3. A method according to claim 1
further including the step of distributing liquid about the microporous pad while applying the electromagnetic energy.

4. A method according to claim 1
further including the step of sensing temperature while applying the electromagnetic energy.

5. A method according to claim 4
wherein the temperature sensing step includes sensing temperature of dermal tissue beneath the epidermal tissue region.

6. A device for applying electromagnetic energy to skin comprising:
a carrier,
an array of electrodes on the carrier connectable to a source of electromagnetic energy to apply the electromagnetic energy,
a microporous pad on the carrier overlying the array of electrodes forming an interior chamber to contain an electrically conductive material, the microporous pad adapted, in use, to contact an epidermal skin region and ionically transport the applied electromagnetic energy to ohmically heat dermal tissue beneath the epidermal skin region, and
at least one temperature sensing probe on the carrier and located outside the microporous pad.

7. A device for applying electromagnetic energy to skin comprising:
a carrier,
an array of electrodes on the carrier connectable to a source of electromagnetic energy to apply the electromagnetic energy,
a microporous pad on the carrier overlying the array of electrodes forming an interior chamber to contain an electrically conductive material, the microporous pad adapted, in use, to contact an epidermal skin region and ionically transport the applied electromagnetic energy to ohmically heat dermal tissue beneath the epidermal skin region, and
at least one temperature sensing probe on the carrier and sized to extend into dermal tissue when the microporous pad contacts the epidermal tissue region.

8. A method for applying electromagnetic energy to skin comprising the steps of:
providing a carrier, an array of electrodes on the carrier connectable to a source of electromagnetic energy to apply the electromagnetic energy, the electrodes being sized so that, while the carrier contacts an epidermal skin region, the electrodes extend into tissue beneath the epidermal skin region,
placing the carrier in contact with an epidermal skin region while applying the electromagnetic energy with the electrodes to ohmically heat tissue beneath the epidermal skin region, and
conveying a liquid through an interior passage in at least some of the electrodes while applying the electromagnetic energy.

9. A method for applying electromagnetic energy to skin comprising the steps of:
providing a carrier, an array of electrodes on the carrier connectable to a source of electromagnetic energy to apply the electromagnetic energy, the electrodes being sized so that, while the carrier contacts an epidermal skin region, the electrodes extend into tissue beneath the epidermal skin region,
placing the carrier in contact with an epidermal skin region while applying the electromagnetic energy with the electrodes to ohmically heat tissue beneath the epidermal skin region, and
sensing temperature while applying the electromagnetic energy.

10. A method according to claim 9
wherein the temperature sensing step includes sensing temperature of dermal tissue beneath the epidermal tissue region.

* * * * *